(12) United States Patent
Porter et al.

(10) Patent No.: US 8,002,547 B2
(45) Date of Patent: Aug. 23, 2011

(54) PREPARATION COPING FOR CREATING AN ACCURATE PERMANENT POST TO SUPPORT A FINAL PROSTHESIS AND METHOD FOR CREATING THE SAME

(75) Inventors: Stephan S. Porter, West Palm Beach, FL (US); Theodore M. Powell, Jupiter, FL (US); Daniel Y. Sullivan, McLean, VA (US)

(73) Assignee: Biomet 3I LLC, Palm Beach Gardens, FL (US)

( * ) Notice: Subject to any disclaimer, the term of this patent is extended or adjusted under 35 U.S.C. 154(b) by 545 days.

(21) Appl. No.: 10/837,803

(22) Filed: May 3, 2004

(65) Prior Publication Data

US 2004/0209227 A1    Oct. 21, 2004

Related U.S. Application Data

(63) Continuation of application No. 09/761,920, filed on Jan. 17, 2001, now Pat. No. 6,758,672.

(60) Provisional application No. 60/176,577, filed on Jan. 18, 2000.

(51) Int. Cl.
*A61C 8/00* (2006.01)

(52) U.S. Cl. .................... 433/173; 433/214

(58) Field of Classification Search .................. 433/173, 433/174, 213, 214
See application file for complete search history.

(56) References Cited

U.S. PATENT DOCUMENTS

| | | |
|---|---|---|
| 3,304,608 A | 2/1967 | Frohnecke |
| 3,958,471 A | 5/1976 | Müller ............................. 82/1 C |
| 4,011,602 A | 3/1977 | Rybicki et al. ..................... 3/1.9 |
| 4,086,701 A | 5/1978 | Kawahara et al. ............. 32/10 A |
| 4,177,562 A | 12/1979 | Miller et al. ................... 433/173 |
| 4,253,833 A | 3/1981 | Edelman ........................ 433/173 |
| 4,306,862 A | 12/1981 | Knox .............................. 433/77 |

(Continued)

FOREIGN PATENT DOCUMENTS

CH    679117 A5    12/1991

(Continued)

OTHER PUBLICATIONS

Exhibit A, drawing of a healing abutment, 1 page (no date).

(Continued)

*Primary Examiner* — Ralph A Lewis

(74) *Attorney, Agent, or Firm* — Nixon Peabody LLP

(57) ABSTRACT

An implant comprising an internal bore having an opening at one end of the implant is initially fixed within a patient's mouth. A support post on which a final artificial prosthesis will be mounted is attached to the implant by allowing a portion of the post to extend into and attach within the bore of the implant. The post generally extends supragingivally from a base at or beneath the gum surface and contains a retention bulb to assist in registering the axial orientation of an impression cap and the final prosthesis. The impression cap is then placed over the post to assist in taking an impression of the relevant dental region. The impression cap contains means to allow to the retention bulb to snap onto the impression cap. After the impression material is placed to surround the impression cap, post and implant, the impression material and impression cap are removed. A healing cap is placed on the post and acts as a temporary tooth able to last within the patient's mouth for several months.

36 Claims, 11 Drawing Sheets

U.S. PATENT DOCUMENTS

| | | | |
|---|---|---|---|
| 4,341,312 A | 7/1982 | Scholer | 211/60 T |
| 4,483,675 A | 11/1984 | Marshall | 433/141 |
| 4,547,157 A | 10/1985 | Driskell | 433/173 |
| 4,575,340 A | 3/1986 | Lustig | 433/173 |
| 4,624,673 A | 11/1986 | Meyer | 623/16 |
| 4,708,654 A | 11/1987 | Branemark | 433/213 |
| 4,713,003 A | 12/1987 | Symington et al. | 433/173 |
| 4,713,004 A | 12/1987 | Linkow et al. | 433/174 |
| 4,722,688 A | 2/1988 | Lonca | 433/173 |
| 4,738,623 A | 4/1988 | Driskell | 433/173 |
| 4,744,753 A | 5/1988 | Ross | 433/173 |
| D296,362 S | 6/1988 | Branemark | D24/33 |
| 4,758,161 A | 7/1988 | Niznick | 433/173 |
| 4,763,788 A | 8/1988 | Jorneus et al. | 206/438 |
| 4,767,331 A | 8/1988 | Hoe | 433/213 |
| 4,772,204 A | 9/1988 | Söderberg | 433/174 |
| 4,826,434 A | 5/1989 | Krueger | 433/173 |
| 4,842,518 A | 6/1989 | Linkow et al. | 433/174 |
| 4,850,870 A | 7/1989 | Lazzara et al. | 433/174 |
| 4,850,873 A | 7/1989 | Lazzara et al. | 433/220 |
| 4,856,994 A | 8/1989 | Lazzara et al. | 433/173 |
| 4,872,839 A | 10/1989 | Brajnovic | 433/173 |
| 4,955,811 A | 9/1990 | Lazzara et al. | 433/173 |
| 4,960,381 A | 10/1990 | Niznick | 433/174 |
| 4,988,297 A | 1/1991 | Lazzara et al. | 433/173 |
| 4,988,298 A | 1/1991 | Lazzara et al. | 433/173 |
| 4,995,810 A | 2/1991 | Söderberg | 433/141 |
| 5,000,685 A | 3/1991 | Brajnovic | 433/173 |
| 5,006,069 A | 4/1991 | Lazzara et al. | 433/173 |
| 5,015,186 A | 5/1991 | Detsch | 433/173 |
| 5,022,860 A | 6/1991 | Lazzara et al. | 433/174 |
| 5,026,285 A | 6/1991 | Durr et al. | 433/173 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,055,047 A | 10/1991 | Names | 433/214 |
| 5,061,181 A | 10/1991 | Niznick | 433/174 |
| 5,062,800 A | 11/1991 | Niznick | 433/229 |
| 5,071,351 A | 12/1991 | Green, Jr. et al. | 433/173 |
| 5,073,111 A | 12/1991 | Daftary | 433/173 |
| 5,100,323 A | 3/1992 | Friedman et al. | 433/173 |
| 5,104,318 A | 4/1992 | Piche et al. | 433/174 |
| 5,106,300 A | 4/1992 | Voitik | 433/173 |
| 5,116,225 A | 5/1992 | Riera | 433/173 |
| 5,122,059 A | 6/1992 | Dürr et al. | 433/173 |
| 5,125,839 A | 6/1992 | Ingber et al. | 433/169 |
| 5,125,841 A | 6/1992 | Carlsson et al. | 433/213 |
| 5,135,395 A | 8/1992 | Marlin | 433/174 |
| 5,145,371 A | 9/1992 | Jörnéus | 433/173 |
| 5,145,372 A | 9/1992 | Daftary et al. | 433/173 |
| 5,145,612 A | 9/1992 | Reay et al. | 261/79.2 |
| 5,154,612 A | 10/1992 | Carlsson et al. | 433/173 |
| 5,171,755 A | 12/1992 | Kaufman et al. | 514/749 |
| 5,188,800 A | 2/1993 | Green, Jr. et al. | 422/23 |
| 5,195,891 A | 3/1993 | Sule | 433/173 |
| 5,195,892 A | 3/1993 | Gersberg | 433/174 |
| 5,199,873 A | 4/1993 | Schulte et al. | 433/174 |
| 5,205,745 A | 4/1993 | Kamiya et al. | 433/173 |
| 5,209,659 A | 5/1993 | Friedman et al. | 433/173 |
| 5,209,666 A | 5/1993 | Balfour et al. | 433/173 |
| 5,213,498 A | 5/1993 | Pelerin | 433/37 |
| 5,213,502 A | 5/1993 | Daftary | 433/172 |
| 5,246,370 A | 9/1993 | Coatoam | 433/173 |
| 5,259,759 A | 11/1993 | Jorneus et al. | 433/173 |
| 5,281,140 A | 1/1994 | Niznick | 433/172 |
| 5,286,195 A | 2/1994 | Clostermann | 433/172 |
| 5,292,252 A | 3/1994 | Nickerson et al. | 433/173 |
| 5,297,963 A | 3/1994 | Dafatry | 433/172 |
| 5,302,125 A | 4/1994 | Xownacki et al. | 433/172 |
| 5,316,476 A | 5/1994 | Krauser | 433/173 |
| 5,316,477 A | 5/1994 | Calderon | 433/173 |
| 5,322,443 A | 6/1994 | Beaty | 433/141 |
| 5,328,371 A | 7/1994 | Hund et al. | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,350,297 A * | 9/1994 | Cohen | 433/76 |
| 5,350,302 A | 9/1994 | Marlin | 433/174 |
| 5,362,234 A | 11/1994 | Salazar et al. | 433/169 |
| 5,362,235 A | 11/1994 | Daftary | 433/172 |
| 5,362,237 A | 11/1994 | Chalifoux | 433/220 |
| 5,368,483 A | 11/1994 | Sutter et al. | 433/173 |
| 5,376,004 A | 12/1994 | Mena | 433/173 |
| 5,399,090 A | 3/1995 | Padros-Fradera | 433/173 |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,433,606 A | 7/1995 | Niznick et al. | 433/173 |
| 5,437,550 A | 8/1995 | Beaty et al. | 433/141 |
| 5,437,551 A | 8/1995 | Chalifoux | 433/173 |
| 5,458,488 A | 10/1995 | Chalifoux | 433/173 |
| 5,476,382 A | 12/1995 | Daftary | 433/172 |
| 5,476,383 A | 12/1995 | Beaty et al. | 433/214 |
| 5,478,237 A | 12/1995 | Ishizawa | 433/201.1 |
| 5,489,210 A | 2/1996 | Hanosh | 433/173 |
| 5,492,471 A | 2/1996 | Singer | 433/172 |
| 5,503,558 A | 4/1996 | Clokie | 433/173 |
| 5,533,898 A | 7/1996 | Mena | 433/173 |
| 5,538,426 A | 7/1996 | Harding et al. | 433/172 |
| 5,547,377 A | 8/1996 | Daftary | 433/172 |
| 5,564,921 A | 10/1996 | Marlin | 433/172 |
| 5,564,923 A | 10/1996 | Grassi et al. | 433/173 |
| 5,564,924 A | 10/1996 | Kwan | 433/173 |
| 5,573,401 A | 11/1996 | Davidson et al. | 433/201.1 |
| 5,588,838 A | 12/1996 | Hansson et al. | 433/173 |
| 5,636,989 A | 6/1997 | Somborac et al. | 433/173 |
| 5,639,237 A | 6/1997 | Fontenot | 433/173 |
| 5,642,996 A | 7/1997 | Mochida et al. | 433/174 |
| 5,651,675 A | 7/1997 | Singer | 433/172 |
| 5,662,475 A | 9/1997 | Mena | 433/172 |
| 5,662,476 A | 9/1997 | Ingber et al. | 433/213 |
| 5,674,069 A | 10/1997 | Osorio | 433/172 |
| 5,674,071 A | 10/1997 | Beaty et al. | 433/172 |
| 5,674,073 A | 10/1997 | Ingber et al. | 433/213 |
| 5,683,249 A | 11/1997 | Ibsen et al. | 433/201.1 |
| 5,685,715 A | 11/1997 | Beaty et al. | 433/173 |
| 5,688,123 A | 11/1997 | Meiers et al. | 433/173 |
| 5,695,336 A | 12/1997 | Lazzara et al. | 433/173 |
| 5,702,346 A | 12/1997 | Lazzara et al. | 433/173 |
| 5,709,547 A | 1/1998 | Lazzara et al. | 433/174 |
| 5,725,375 A | 3/1998 | Rogers | 433/172 |
| 5,727,943 A | 3/1998 | Beaty et al. | 433/174 |
| 5,733,124 A | 3/1998 | Kwan | 433/173 |
| 5,749,732 A | 5/1998 | Sendax | 433/174 |
| 5,752,830 A | 5/1998 | Suarez | 433/173 |
| 5,759,034 A | 6/1998 | Daftary | 433/173 |
| 5,762,500 A | 6/1998 | Lazarof | 433/213 |
| 5,779,480 A | 7/1998 | Groll et al. | 433/173 |
| 5,782,637 A | 7/1998 | Cosenza | 433/173 |
| 5,782,918 A | 7/1998 | Klardie et al. | 623/16 |
| 5,788,494 A | 8/1998 | Phimmasone | 433/213 |
| 5,816,809 A | 10/1998 | Sapkos | 433/172 |
| 5,823,777 A | 10/1998 | Misch et al. | 433/174 |
| 5,829,977 A | 11/1998 | Rogers et al. | 433/172 |
| 5,829,981 A | 11/1998 | Ziegler | 433/214 |
| 5,842,864 A | 12/1998 | Unger | 433/172 |
| 5,846,079 A | 12/1998 | Knode | 433/213 |
| 5,868,572 A | 2/1999 | Lazzara et al. | 433/173 |
| 5,873,722 A | 2/1999 | Lazzara et al. | 433/173 |
| 5,873,727 A | 2/1999 | Barlow | 434/128 |
| 5,879,161 A | 3/1999 | Lazzara | 433/173 |
| 5,899,695 A | 5/1999 | Lazzara et al. | 433/173 |
| 5,899,697 A | 5/1999 | Lazzara et al. | 433/173 |
| 5,904,483 A | 5/1999 | Wade | |
| 5,927,979 A | 7/1999 | Misch et al. | 433/173 |
| 5,934,906 A | 8/1999 | Phimmasone | 433/172 |
| 5,938,443 A | 8/1999 | Lazzara et al. | 433/173 |
| 5,944,525 A | 8/1999 | Ura | 433/173 |
| 5,947,736 A | 9/1999 | Behrend | 433/214 |
| 5,964,591 A | 10/1999 | Beaty et al. | 433/173 |
| 6,068,478 A | 5/2000 | Grande et al. | 433/172 |
| 6,068,480 A | 5/2000 | Misch et al. | 433/173 |
| 6,083,004 A | 7/2000 | Misch et al. | 433/173 |
| 6,120,293 A | 9/2000 | Lazzara et al. | 433/173 |
| 6,142,782 A | 11/2000 | Lazarof | 433/173 |
| 6,149,433 A | 11/2000 | Ziegler et al. | 433/214 |

| | | | |
|---|---|---|---|
| 6,155,828 A | 12/2000 | Lazzara et al. | 433/173 |
| 6,159,010 A | 12/2000 | Rogers et al. | 433/172 |
| 6,217,331 B1 | 4/2001 | Rogers et al. | 433/173 |
| 6,227,856 B1 | 5/2001 | Beaty et al. | 433/172 |
| 6,247,932 B1 | 6/2001 | Sutter | 433/173 |
| 6,276,938 B1 | 8/2001 | Jorneus et al. | 433/172 |
| 6,332,777 B1 | 12/2001 | Sutter | 433/173 |
| 6,488,501 B1 | 12/2002 | Harding | 433/173 |
| 6,655,962 B1 * | 12/2003 | Kennard | 433/174 |
| 6,758,672 B2 * | 7/2004 | Porter et al. | 433/173 |

FOREIGN PATENT DOCUMENTS

| | | |
|---|---|---|
| DE | 1 232 314 | 1/1967 |
| DE | 1 541 225 | 4/1970 |
| DE | 21 14 323 | 10/1971 |
| DE | 31 10 694 | 9/1982 |
| DE | 31 10693 A1 | 9/1982 |
| DE | 35 31 389 A1 | 3/1987 |
| DE | 40 28 855 A1 | 3/1992 |
| DE | 197 42 381 | 2/1999 |
| EP | 0 190 670 A2 | 8/1986 |
| EP | 0 442 855 A1 | 8/1991 |
| EP | 0 473 262 | 3/1992 |
| EP | 0 657 146 A1 | 6/1995 |
| EP | 0 727 193 A1 | 8/1996 |
| EP | 0 814 724 B1 | 1/1998 |
| EP | 0 879 025 B1 | 11/1998 |
| FR | 1463860 | 7/1965 |
| GB | 1 291 470 | 10/1972 |
| GB | 2 252 501 A | 8/1992 |
| WO | WO 85/02337 | 6/1985 |
| WO | WO 88/03007 | 5/1988 |
| WO | WO 93/20774 | 10/1993 |
| WO | WO 96/19946 | 7/1996 |
| WO | WO 96/19947 | 7/1996 |
| WO | WO 96/29019 | 9/1996 |
| WO | WO 96/29020 | 9/1996 |
| WO | WO 97/01306 | 1/1997 |
| WO | WO 97/28756 | 1/1997 |
| WO | WO 97/06930 | 2/1997 |
| WO | WO 97/14371 | 4/1997 |
| WO | WO 97/20518 | 6/1997 |
| WO | WO 97/27816 | 8/1997 |
| WO | WO 97/28755 | 8/1997 |
| WO | WO 97/28756 | 8/1997 |
| WO | WO 98/31296 | 7/1998 |
| WO | WO 98/32393 | 7/1998 |
| WO | WO 98/36701 | 8/1998 |
| WO | WO 98/52490 | 11/1998 |
| WO | WO 99/04723 | 2/1999 |
| WO | WO 99/29255 | 6/1999 |
| WO | WO 99/62421 * | 12/1999 |
| WO | WO 02/17814 A1 | 3/2002 |

OTHER PUBLICATIONS

Exhibit B, assembly drawing of a coping and the component drawings which comprise the coping assembly, 3 pages (1989, 1990, 1991).

Adell, R., et al., "A 15-Year Study of Osseointegrated Implants in the Treatment of the Edentulous Jaw," *Int. J. Oral Surg.*, vol. 10, pp. 387-416 (1981).

Astra Tech Inc., "Astra Tech Implants Dental System" Brochure, 21 pages (no date).

Core-Vent® Corporation, "1989 Core-Vent Implant Symposium" Brochure, 2 pages (Mar. 1988).

Impla-Med™ Incorporated, "Come to the Source. The Choice Is Clear." Catalog, 16 pages (Mar. 1991).

Impla-Med, Inc., and Dental Imaging Associates, Inc., "The DIA Anatomic Abutment System™" Brochure, 12 pages (Oct. 1991).

Implant Innovations, Inc., Catalog, 64 pages (Jul. 2, 1990).

Implant Innovations, Inc., Prosthetic Catalog, 66 pages (1991).

Implant Support Systems, Inc., Catalog, 42 pages (Summer 1993).

Imtec Corporation, "Hexed-Head™ Implant System" Catalog, 16 pages (Spring 1993).

Interpore International, "IMZ™ Prosthetic Flow Chart," 2 pages (Jul. 1993).

Lazzara, Richard J., "Managing the Soft Tissue Margin: The Key to Implant Aesthetics," *Practical Periodontics and Aesthetic Dentistry*, vol. 5, No. 5, pp. cover, 81-87 (Jun./Jul. 1993).

Ledermann, Philip D., et al., "The Ha-Ti Implant," *Schweiz Monatsschr Zahnmed*, vol. 101, pp. 611-617 (May 1991).

Lewis, Steven G., et al., "Single Tooth Implant Supported Restorations," *The International Journal of Oral & Maxillofacial Implants*, vol. 3, No. 1, pp. 25-30 (1988).

Lewis, S., et al., "The 'UCLA' Abutment," *The International Journal of Oral & Maxillofacial Implants*, vol. 3, No. 3, pp. 183-189 (1988).

Nobelpharma, "Brånemark System® SmiLine" Catalog, 24 pages (1991).

Oratronics Inc., "Endosseous Tri-Dimensional T-3D Oral Implant Healing System (OIHS)" Brochure, 8 pages (1978).

Perri, George, et al., "Single Tooth Implants," *Journal of the California Dental Association*, vol. 17, No. 3, pp. cover, 30-33 (Mar. 1989).

Steri-Oss Inc., Bio-Esthetic™ Technique Manual, 6 pages (1995).

Steri-Oss Inc., "Osstium" Brochure, 8 pages (Fall 1995).

Steri-Oss Inc., Catalog, 36 pages (Sep. 1990).

Steri-Oss Inc., Catalog, pp. cover, back, 7, 14 (Feb. 1992).

Stryker, Price List, 46 pages (Jun. 1, 1993).

Stryker, "Surgical Flexibility Prosthetic Simplicity" Brochure, 8 pages (no date).

Sutter, Franz, et al., "The New Restorative Concept of the ITI Dental Implant System: Design and Engineering," *The International Journal of Periodontics & Restorative Dentistry*, vol. 13, No. 5, pp. 409-431 (1993).

* cited by examiner

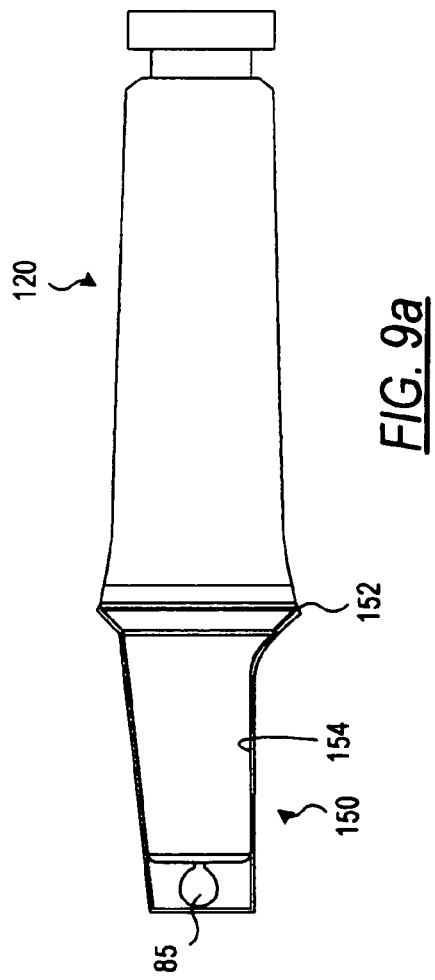
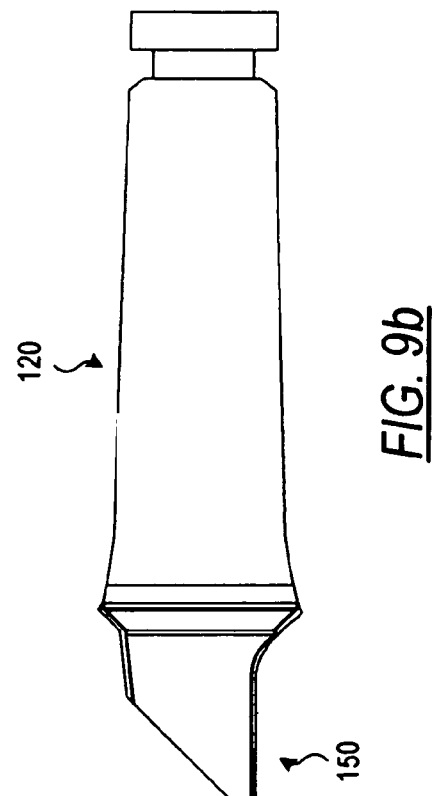

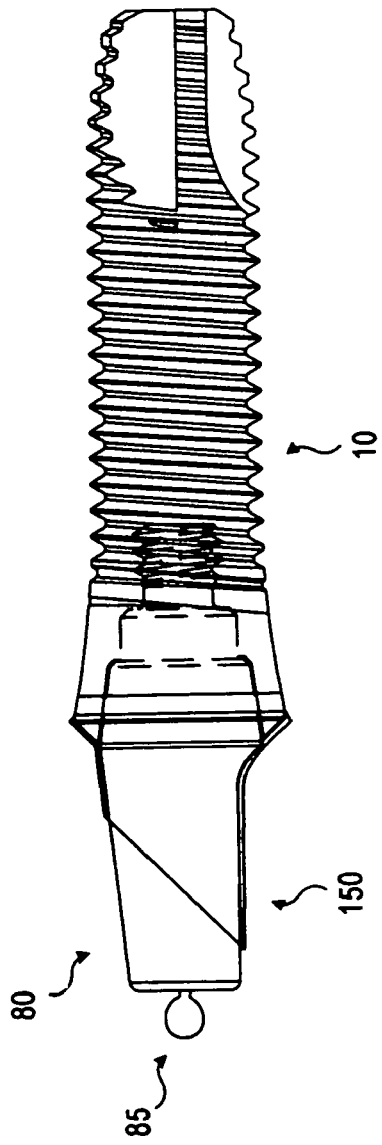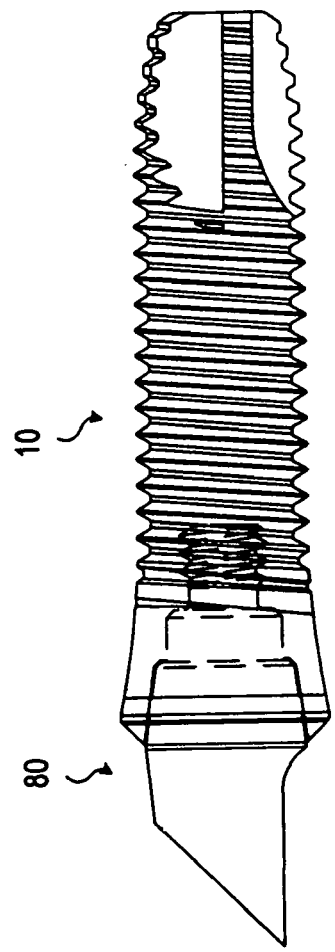

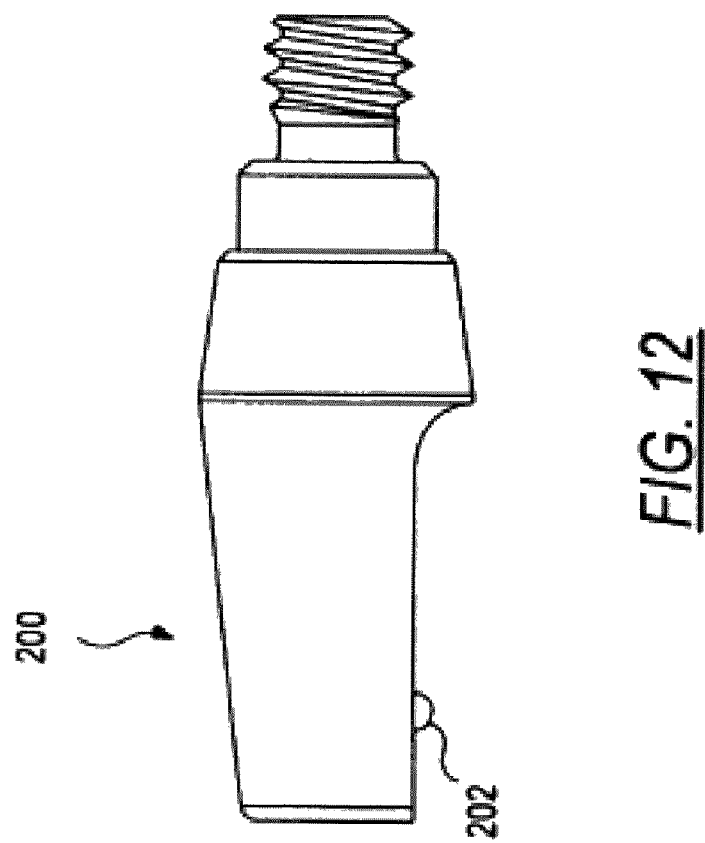
FIG. 12
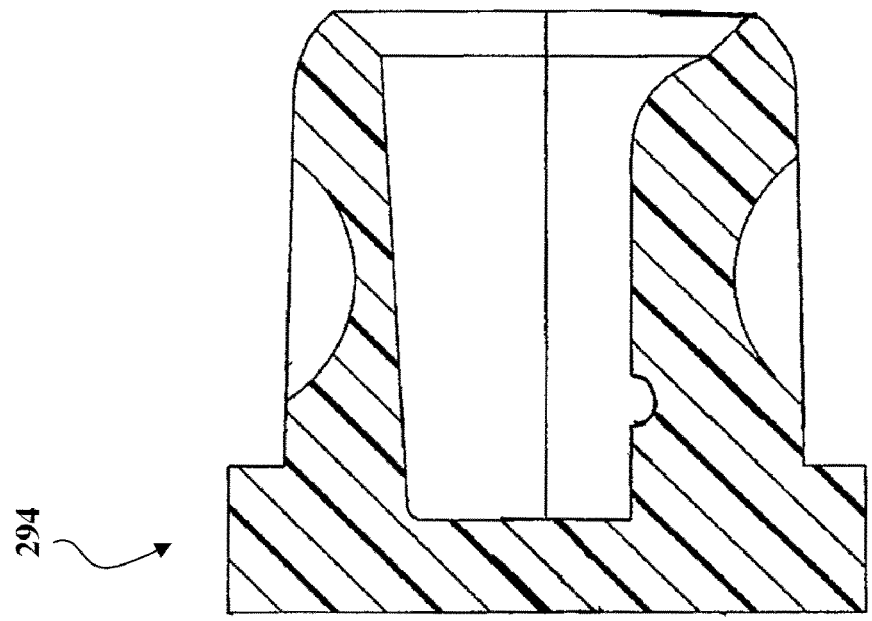

PREPARATION COPING FOR CREATING AN ACCURATE PERMANENT POST TO SUPPORT A FINAL PROSTHESIS AND METHOD FOR CREATING THE SAME

RELATED APPLICATION

This application is a continuation of U.S. patent application Ser. No. 09/761,920, filed Jan. 17, 2001 now U.S. Pat. No. 6,758,672, now allowed; which is based on U.S. Provisional Application No. 60/176,577, filed Jan. 18, 2000, now abandoned.

FIELD OF INVENTION

The present invention relates generally to a temporary addition to a permanent post in a dental implant system. More particularly, the present invention relates to a preparation coping used to accurately prep a permanent post that supports the final prosthesis.

BACKGROUND OF THE INVENTION

It has become fairly common to replace a missing tooth with a prosthetic tooth attached to a dental implant. The prosthetic tooth preferably has a size, color and shape that mimics the missing natural tooth, thus revealing an aesthetically pleasing and structurally sound artificial tooth.

Most current methods by which the prosthetic tooth and implant are completely integrated into the patient's mouth require six to ten months or longer because two distinct, time consuming steps are involved. First, the implant is inserted into the jawbone and covered by suturing the overlying gingival tissue. The implant then osseointegrates with the jawbone for a period of about three to six months. Second, the gingival tissue is reopened and a healing abutment is placed onto the implant. The gingiva is sutured again to allow healing around the implant and healing abutment. The gingiva must heal for a period of approximately four to six weeks. When the prosthetic tooth is eventually placed onto the implant, the gingiva easily conforms around the prosthetic tooth and the overall process is complete.

A single-stage dental implant is typically installed through a ridge in the jawbone that is covered by gingival tissue. The dental implant provides an artificial root on which a prosthetic tooth is mounted to replace a missing tooth that formerly emerged from the jawbone. The single-stage implant comprises an anchoring portion for extending into and integrating with the jawbone and an integral gingival section that extends beyond the ridge of the jawbone. Because the gingival section is integral with the anchoring portion, there is no seam in which bacteria may collect to cause infections.

Single stage implants, or "transgingival" implants, simultaneously promote osseointegration and gingival healing. A lower portion of the transgingival implant integrates with the jawbone and an upper portion of the implant extends through the overlying gingiva such that the gingiva heals therearound. Thus, the four to six week gingival healing period is encompassed in the three to six month osseointegration period. Consequently, the patient is outfitted with a prosthetic tooth in a shorter overall period of time with only one incision into the gingiva being required, reducing the trauma to that dental region and lowering patient costs due to the lower total number of dental procedures.

During the preparation of dental restorations supported on implants embedded in a living jawbone, it is frequently useful to provide a permanent support post connected to the single stage implant. The final prosthesis fits over the support post. To assist in preparing the final prosthesis, a post analog is prepped in the laboratory. It is desirable for the prepped post analog to be identical to the post within the patient's mouth, however an element for creating these identical pieces and a method for creating such an element does not present exist. Thus, a need exists for a preparation coping to create an accurate permanent support post that will support the final prosthesis.

SUMMARY OF THE INVENTION

In accordance with the present invention, an implant comprising an internal bore having an opening at one end of the implant is initially fixed within a patient's mouth. A support post on which a final artificial prosthesis will be mounted is attached to the implant by allowing a portion of the post to extend into and attach within the bore of the implant. The post generally extends supragingivally from a base at or beneath the gum surface and contains a retention bulb to assist in registering the axial orientation of an impression cap and ensuring proper placement of the final prosthesis. The impression cap is placed over the post to assist in taking an impression of the relevant dental region. The impression cap possesses means to allow the retention bulb to snap onto the impression cap. After the impression material is placed to surround the impression cap, post and implant, the impression material and impression cap are removed. A healing cap is placed on the post and acts as a temporary tooth able to last within the patient's mouth for several months.

A post analog is attached to the impression cap that is seated within the impression material. A model can be poured about the post analog, impression cap and impression material to replicate the relevant dental region. The plaster model and the post analog are then removed and a preparation coping is installed over the post analog. The preparation coping assists in properly shaping the post within the mouth. Specifically, the preparation coping and the post analog are simultaneously prepped to effect the form, orientation and shape of the final post. The prepped relief coping is then removed from the post analog and placed over the post. Once the relief coping has been prepped, it is essentially a template that is used for preparing the post in the same manner as the prepped post analog. The prepped post will then be able to properly and accurately receive the overlying final prosthesis that was developed from the prepped post analog.

BRIEF DESCRIPTION OF THE DRAWINGS

The foregoing and other advantages of the invention will become apparent upon reading the detailed description as follows and upon reference to the drawings in which:

FIG. 9a is a side view of a preparation coping installed on post analog;

FIG. 9b is a side view of a prepped preparation coping and prepped post analog;

FIG. 10 is a side view of the prepped preparation coping of FIG. 9b overlying the post of FIG. 4 attached to an implant;

FIG. 11 is a side view of a prepped post attached to an implant; and

FIG. 12 is a side view of a post of an alternative embodiment of the present invention.

Figure 1C:
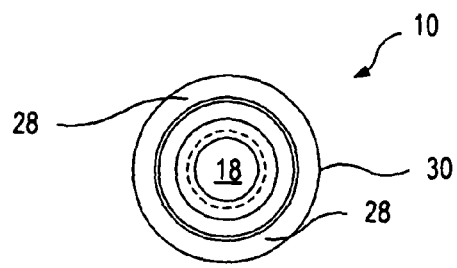
FIGS. 1a-1c are side, insertion end, and gingival end views of an implant according to the present invention.

While the present invention is susceptible to various modifications and alternative forms, specific embodiments have been shown by way of example in the drawings and will herein be described in detail. It should be understood, however, that it is not intended to limit the invention of the particular forms disclosed, but on the contrary, the intention is to cover all modifications, equivalents and alternative falling within the spirit and scope of the invention as defined by the appended claims.

DETAILED DESCRIPTION OF ILLUSTRATIVE EMBODIMENTS

A preparation coping to assist in developing an accurate permanent support post and a method of developing the same has been discovered. Specifically, the preparation coping of the present application replicates the shape and orientation of a prepped post analog and comprises a modifiable cylinder containing an upwardly tapering inner surface for receiving the upper portion of the support post. The support post is tailored by modifying a preparation coping in a manner reflecting the prepping of the post analog and placing the preparation coping on the support post and prepping the post in accordance with the preparation coping.

Figure 1A:
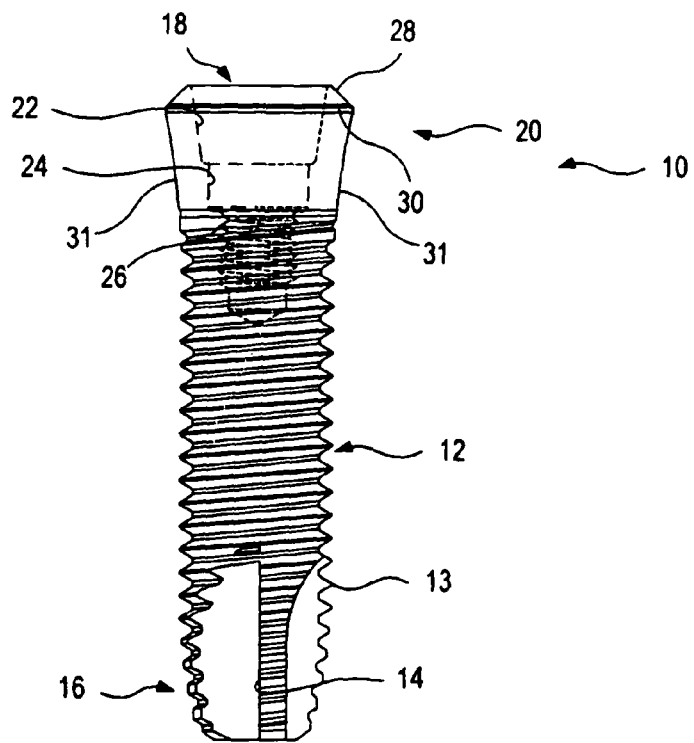
Figure 1B:
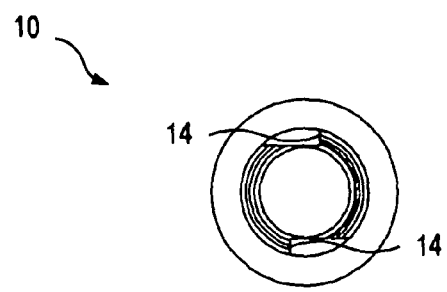

The dental system of the present invention is designed to create an accurate support post comprises, in addition to the preparation coping, a post analog and support post, a dental implant, a cover screw, an impression cap and a healing cap. These elements are referred to and depicted in FIGS. 1-6. Referring specifically now to the figures and initially to FIG. 1a, an implant 10 is illustrated having a main body 12 with a threaded outer surface 13. The threaded outer surface 13 includes a self-tapping region with incremental cutting edges 14 at an apical end 16 of the main body 12. These incremental cutting edges 14 are shown in FIG. 1b and defined in detail in U.S. Pat. No. 5,727,943, entitled "Self-Tapping, Screw-Type Dental Implant", which is herein incorporated by reference in its entirety. An axial opening 18 in a gingival end 20 of the main body 12 of the implant 10 has three distinct zones proceeding from the uppermost edge of the gingival end 20 into the interior of the implant 10, a) an inwardly tapering zone 22, b) a substantially cylindrical zone 24 and c) an internally threaded zone 26.

A cover screw attaches to the implant 10 and is used to protect and envelop the opening 18 of the implant 10 during osseointegration. FIGS. 2a-2d illustrate a cover screw 44 that is inserted into the implant 10. As shown in side view FIG. 2a, the cover screw 44 has a head 46, an externally threaded insertion end 48 and a cylindrical shaft 50 between the head 46 and the insertion end 48.

Figure 2D:
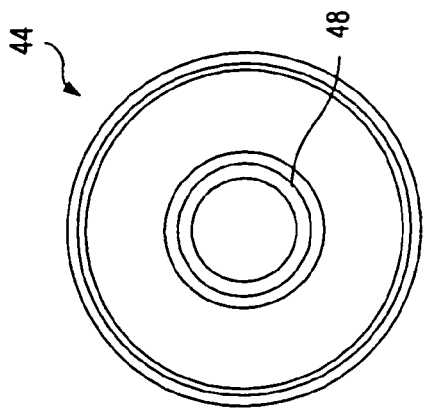
FIGS. 2a-2d are side, section, head end, and insertion end views of a cover screw.
Figure 2A:
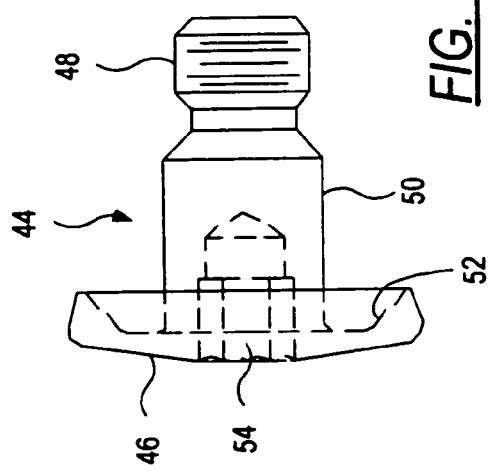
Figure 2B:
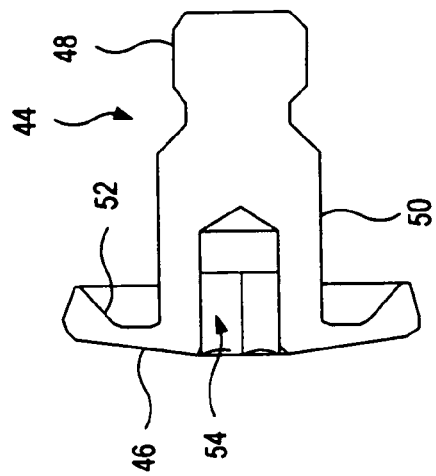
Figure 2C:
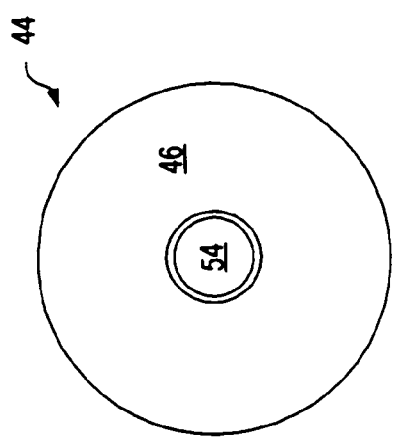

In use, the insertion end 48 of the cover screw 44, as shown in sectional view FIG. 2b and insertion end view FIG. 2d, is threaded into the internally threaded zone to 26 of the opening 18 of the implant 10. The cylindrical shaft 50 fits within the cylindrical zone 24 of the opening 18 of the implant 10. The mating of the cylindrical zone 24 and cylindrical shaft 50 provide stability to the combination of the cover screw 44 and the opening 18. The head 46 has a reentrant under-surface 52 that covers the outer surface 28 of the implant 10, as shown in FIG. 1c, when the cover screw 44 is placed on the implant 10. The head 46 also has a bore 54, as shown in FIG. 2c, for engaging a tool, such as an Allen wrench (not shown), that turns the cover screw 44 into the internally-threaded zone 26 of the implant 10.

Figure 3C:
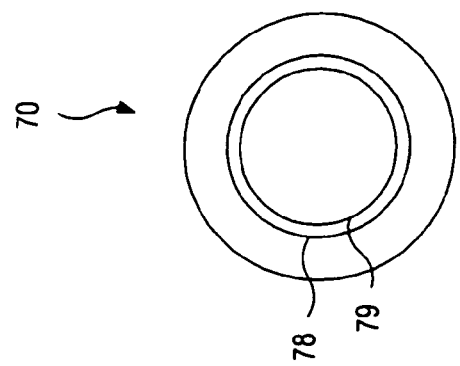
FIGS. 3a-3c are side, head-end, and insertion-end views of a cover screw.
Figure 3A:
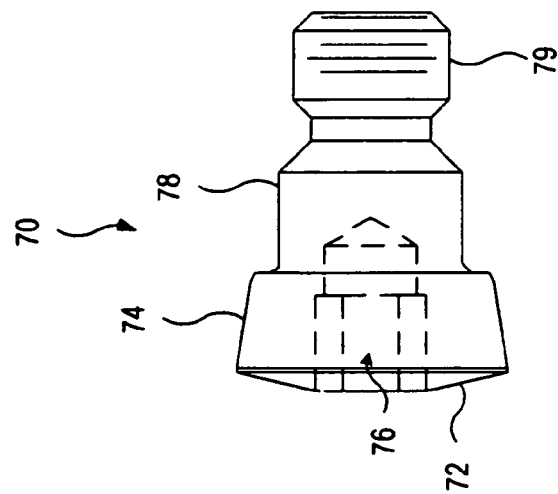
Figure 3B:
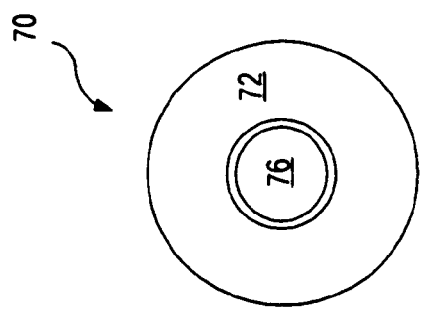

FIGS. 3a-3c illustrate another cover screw 70 of the present invention. Cover screw 70 has a head 72 with a tapering side-surface 74 for engaging the tapered zone 22 of the opening 18 of the implant. The top surface of the head 72 is designed to be approximately flush with the uppermost edge of the gingival end 20 of the implants. The tapering surfaces of the tapered zone 22 and the side-surface 74 are preferably tapered on the same angle suitably to provide a locking taper (e.g., about 18°) when those surfaces are engaged. As shown in FIG. 3a, a cylindrical shaft 78 is placed between the head 72 and a threaded insertion end 79, as illustrated in FIG. 3c. The head 72 has a bore 76, as shown in FIG. 3b, for engaging a wrench that turns the cover screw into the internally-threaded zone 26 of the opening 18.

Figure 4C:
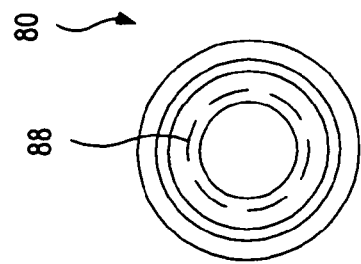
FIGS. 4a-4d are a side view, supragingival end view, insertion end view, and an assembly view of a post and implant for supporting a dental prosthesis.
Figure 4A:
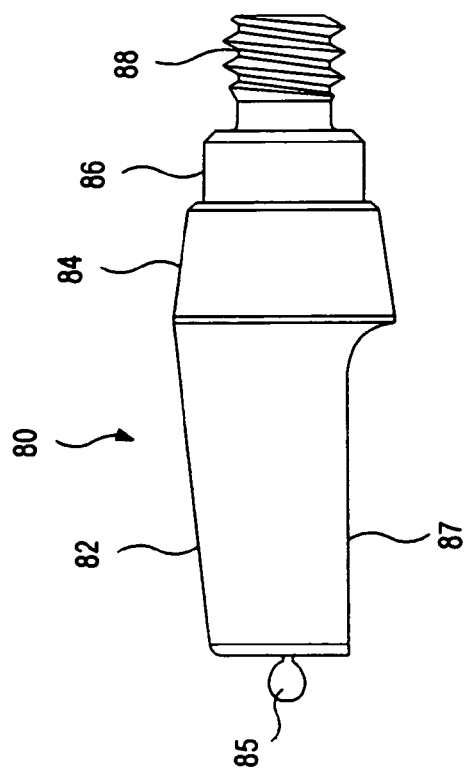
Figure 4B:
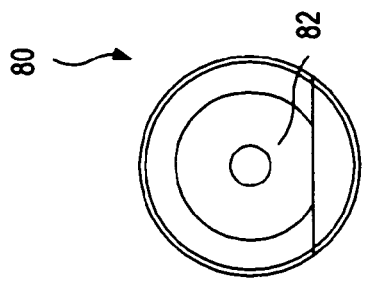

After the implant 10 becomes osseointegrated to the living jawbone, the cover screw 44 or 70 is removed and a post 80, shown in FIGS. 4a-4c, possessing a retention bulb 85 is installed and attached to the implant 10. It is also possible to attach the post 80 to the implant 10, after installation of the implant, without the use of a cover screw. The post 80 includes four zones in a longitudinal sequence, namely, a supragingival zone 82, a locking-taper zone 84, a substantially cylindrical zone 86, and an externally threaded zone 88. The three zones 84, 86 and 88 correspond and mate with the same features, respectively, as the side surface 74, the cylindrical shaft 78 and the insertion end 79 of the cover screw 70 of FIG. 3.

Figure 4D:
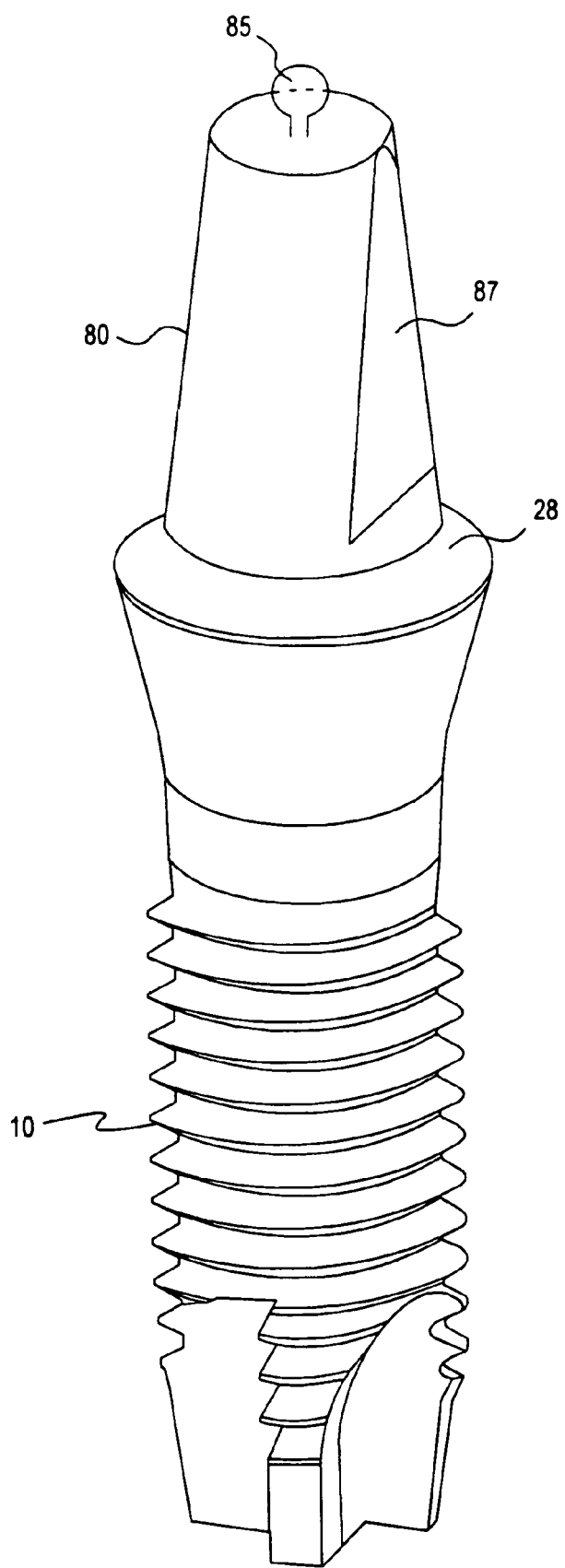

In use, the post 80 is attached to the implant 10, as shown in FIG. 4d, by inserting the externally-threaded zone 88 into the internally-threaded zone 26 of the opening 18 and rotating the post 80 until the tapered zones 84 and 22 engage and lock together. During the process of turning the post 80 into the implant, the cylindrical zones 24 and 86 provide axial stability to prohibit cross-threading the threaded surfaces of zones 88 and 26. The axial stability also provides for true engagement of the tapering surfaces 84 and 22. FIGS. 4a and 4d also display the supragingival zone 82 having a flat surface 87 that is useful to prevent a cemented final prosthesis from rotating after insertion on the post 80.

To ensure that the tapering surfaces 84 and 22 do not resist in providing the required axial tension from the engagement of the threaded portions 88 and 26, the tapering surfaces 84 and 22 may be provided with a lubricant to reduce the friction between them. For example, one or both of the tapering surfaces 84 and 22 may have a gold layer to assist in free rotation.

Figure 5A:
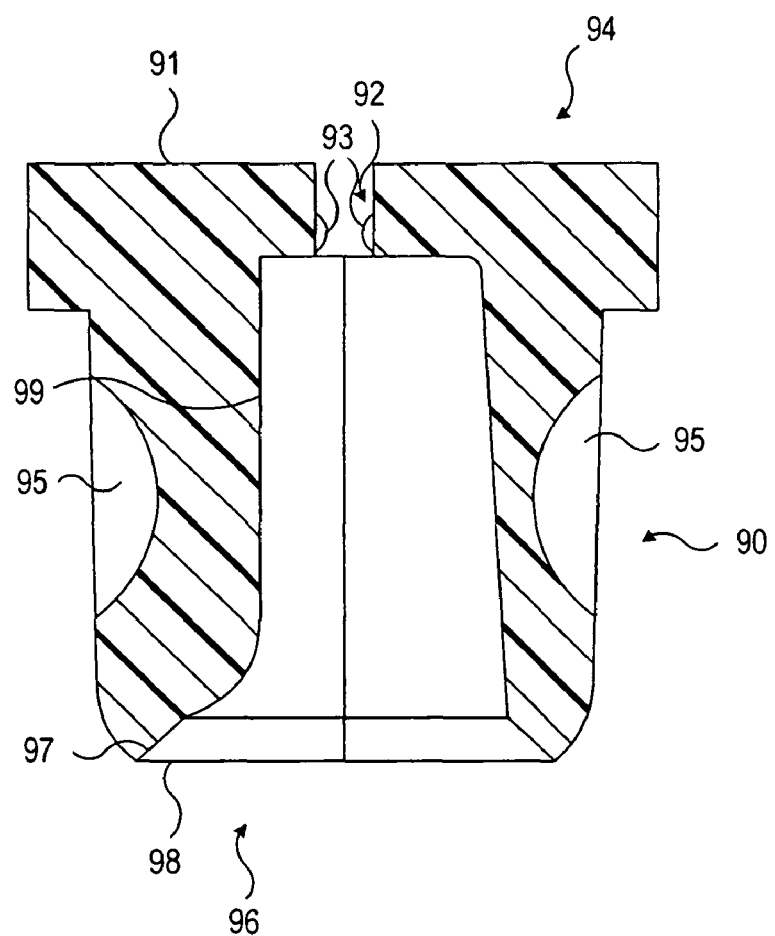
FIG. 5a is a longitudinal sectional view taken through the middle of an impression cap.
Figure 5B:
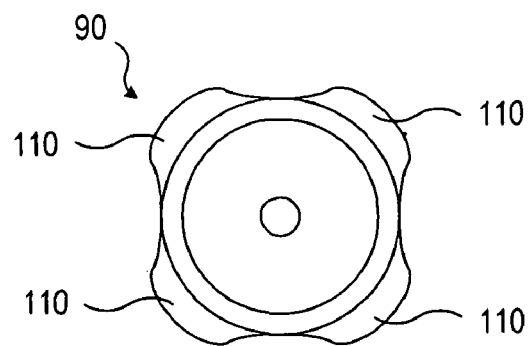
FIG. 5b is a head-end view of an impression cap.
Figure 8:
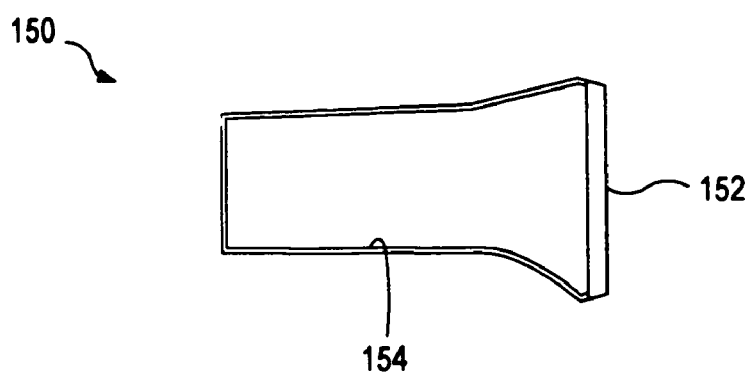
FIG. 8 is a side view of a preparation coping of the present invention.

To take an impression of the relevant dental region within the patient's mouth, an impression cap 90 is installed on the post 80. The impression cap 90, as shown in FIGS. 5a-5b, has generally cylindrically shaped outer side walls, a tapered inner side wall and a flat inner side wall 99. The flat inner side wall 99 corresponds to the flat outer side wall of the post 80, as shown in FIG. 4a, and the post analog 120, as shown in FIG. 8, to prevent rotation of the impression cap 90. The impression cap 90 has an open bottom 96 bounded by a lowermost rim 98 enclosing an annular shoulder 97. The outer side wall turns inward at the bottom toward the rim 98. It its top 94, the impression cap 90 has a top wall 91 with a contoured hole 92 therethrough. The width of the contoured hole 92 is about the same width as the retention bulb 85 of the post 80 that is placed into the hole 92 of the impression cap 90. The retention bulb 85, disposed on top of the post 80, is designed to fit snugly within the hole 92 in the top wall 91 of the impression cap 90. A dentist can easily determine if the retention bulb is correctly seated by noting the position of the retention bulb. Further, a dentist can immediately determine if the impression coping has shifted during the impressioning process. The side walls of the hole 92 contain expansions 93 and provide axial retention after the post 80 is inserted through the impression cap 90 and into the hole 92. Thus, the combination of the retention bulb 85 and the hole 92 register the axial position of the impression cap 90 on the post 80. The impression cap 90 contains grooves 95 to further assist in rotational retention when the impression cap 90 is placed within impression material (not shown). The impression cap 90 is preferably made of a resilient polymeric material that retains its shape, such as, for example, Delrin® made by E. I. du Pont de Nemours and Company of Wilmington, Del.

A head-end view of the impression cap 90 is shown in FIG. 5b. After insertion of the impression cap 90 onto and over the post 80 so that the impression cap in 90 grasps the post 80 by at least the retention bulb 85, the dentist may, to facilitate insertion of the impression cap 90, prep one or more of the leaves 110 extending from the top surface of the impression cap 90. The leaves 110 assist in maintain the axial position of the impression cap 90 within the impression material.

Figure 6:
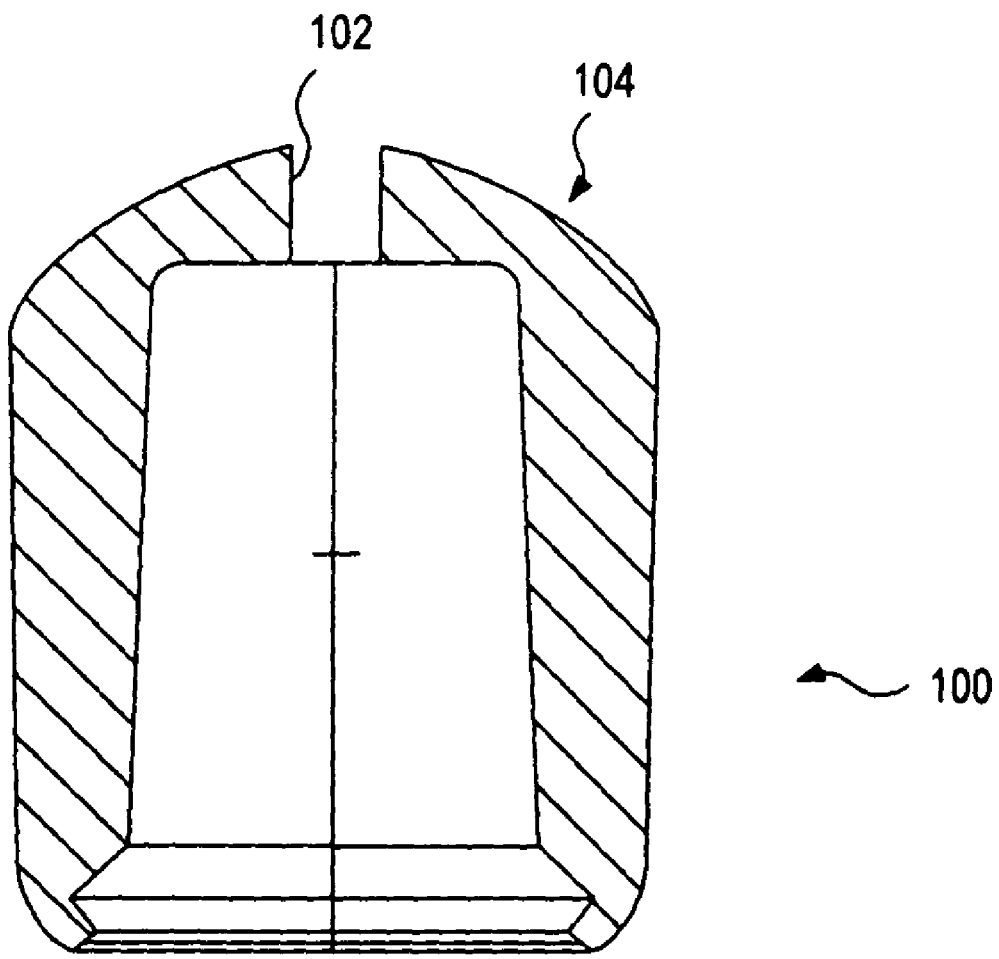
FIG. 6 is a longitudinal sectional view taken through the middle of a healing cap.

An impression of the dental region assists the dentist to accurately create and construct an artificial tooth. To take an impression, impression material is added to the dental region and allowed to form around the implant 10, post 80, and impression cap 90. The impression material is then removed together with the impression cap 90. At the site where the impression cap 90 was disposed, a healing cap 100, as shown in FIG. 6, is then installed to engage the post 80 that is attached to the implant 10. The healing cap 100, which contains a hole 102 through its dome-shaped top 104, is designed to act as a temporary tooth that is cosmetically pleasing and able to last within the patient's mouth for several months. It is contemplated in accordance with the present invention that the hole 102 of the healing cap 100 can contain expansions similar to the expansions 93 of the impression cap 90, as shown in FIG. 5a, to provide axial retention.

Figure 7:
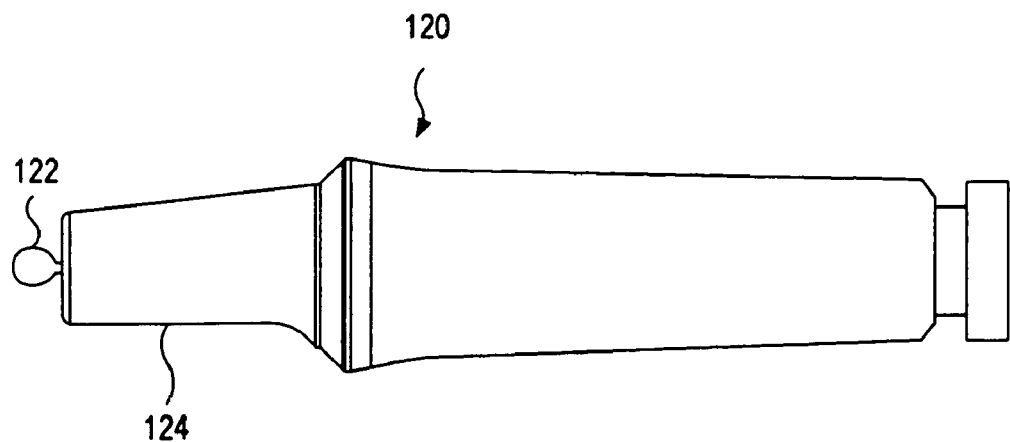
FIG. 7 is a side view of a post analog.

A post analog 120 with a retention bulb 122 and a flat surface 124 similar to the flat surface 87 of the post 80, as shown in FIG. 7, is then installed, usually in a laboratory, into the impression material and attached to the impression cap 90 that is set within the impression material. The post analog 120 is a device that mimics the external shape of the upper portion of an implant and post but is designed to be retained in a plaster cast. A model (using, for example, cement) is poured about the post analog 120, impression cap 90 and impression material to replicate the dental region surrounding the location that the permanent post will be located. The impression material and the impression cap 90 are then removed to reveal the model of the patient's mouth and the attached post analog 120.

It has been discovered that the use of a preparation coping 150 (see FIGS. 8 and 9a) installed on top of the post analog 120 after the impression material and the impression cap 90 are removed will assist in properly shaping the post 80 in the mouth. The preparation coping 150 is formed from plastic (e.g. polyoxmethylene), metal or substantially any polymeric material that allows the clinician to form and shape (i.e., "prep") the upper region of the post analog 120 and preparation coping 150 simultaneously. The preparation coping 150 and post analog 120 permit accurate preparation of the post 80 and provide positive verification that the post 80 is prepared correctly. It is preferable that the preparation coping 150 is disposed on the post analog 120 during the prepping procedure. However, it is contemplated that the post analog 120 can be first prepped while the preparation coping 150 is not on the post analog 120. Then, the prepped preparation coping 150 can be attached to the prepped post analog 120 so that the preparation coping 150 can be prepped substantially identical to the post analog 120. A flat internal surface 154 of the preparation coping 150 corresponds to the external flat surface 124 of the post analog 120 and further provides means to prevent rotation of the preparation coping 150 while disposed on the post analog 120 and the post 80.

Specifically, as shown in FIG. 9a, the plastic preparation coping 150 fits over the top of the post analog 120 and closely interfits along an entire length of the post analog 120. The lower rim 152 of the plastic preparation coping 150 tightly interfits around the edges of the maximum diameter region of the post analog 120 to secure the plastic preparation coping 150 to the post analog 120. Alternatively, it is contemplated in accordance with the present invention that the inner dimensions of the preparation coping 150 can be the same or slightly less than the post analog 120. It is also contemplated in accordance with the present invention that the preparation coping 150 can grasp onto the rim of the post analog 120 or the undercut below the major diameter of the post analog 120.

The compilation of the post analog 120 and plastic preparation coping 150 are then prepped to substantially fit within the adjacent natural teeth in the patient's mouth. As shown in FIG. 9b, to properly prepare the above-mentioned compilation of components, the post analog 120 and plastic preparation coping 150 are prepped such that the final prosthesis to be supported by the post 80 is at the proper shape, angle, and displacement to fit within the adjacent teeth in the patient's mouth. After prepping, the laboratory develops the final prosthesis.

The final prosthesis and "prepped" preparation coping 150 are shipped to the dentist who removes the protective healing cap and places the prepped preparation coping 150 on the post 80 overlying the implant 10 within the patient's mouth. The post closely interfits along an entire length of the post 80. The post 80 will extend through the prepped preparation coping 150, as shown in FIG. 10. The post 80 will subsequently be prepped, using the preparation coping 150 as a template, such that the prepped post 80 presents the same shape, angle and displacement as the preparation to coping 150. The final implant 10 and prepped overlying post 80 are shown in FIG. 11. It is contemplated in accordance with the present invention that the top surface of the prepped post 80 is substantially identical to the top surface of the post analog 120.

Occasionally, the top surface of the post 80 will be prepped such that the final prosthesis does not properly align with the top surface of the post 80. This situation may arise, for example, if the post analog 120 is prepped with a flat top surface and the final prosthesis is created to mimic the flat top surface of the post analog, but the post 80 within the patient's mouth is improperly prepped to contain a slight protruding bump or pimple, the final prosthesis will not seat properly on the post 80. To avert this undesirable situation, two preventative measures can be undertaken. First, the laboratory can prep the top surface of the post analog to contain a bump or pimple such that the final prosthesis will contain a depression or dimple. The depression or dimple in the final prosthesis created from this post analog will be able to receive a post 80 that is outwardly formed and still allow the final prosthesis to seat properly on top of the post 80. Secondly, the top surface of each post 80 can be prepped with a depression or dimple such that a final prosthesis created with a protruding surface will seat properly on top of the post 80.

In an alternate embodiment, it is contemplated in accordance with the present invention that a retention bump 202 exists on a side wall, as shown in FIG. 12, of a post 200 to provide axial retention and prevent rotation of any overlying components (e.g., an impression coping 294, preparation coping, or healing cap). It is further contemplated that the retention bump 202 can be located anywhere circumferentially on the post 200. Disposing the retention bump 202 on a side wall of the post 200 will allow a reduced profile post as compared to the post with the retention bump on the top of the post.

It is contemplated in accordance with the present invention that several of the components in the dental system described herein can be color-coded. Specifically, each post, impression cap and post analog can be coded to indicate the size of each component. For example, a set of components (i.e., the post, impression cap and post analog) having the same diameter (e.g., 4 mm) will be coded the same color. Components of a differing diameter (e.g., 5.5 mm and 7 mm) will be coded different colors.

While the present invention has been described with reference to the particular embodiments illustrated, those skilled in the art will recognize that many changes and to variations may be made thereto without departing from the spirit and scope of the present invention. The embodiments and obvious variations thereof are contemplated as falling within the scope and spirit of the claimed invention, which is set forth in the following claims:

What is claimed is:

1. An implant-abutment system, comprising:
   a post adapted to extend supragingivally, the post having a tapered external surface with a flat portion; and
   an impression coping including:
   an uppermost surface having at least one radially extending flange for being received within impression material;
   a lowermost surface;
   an internal surface located between the uppermost and lowermost surfaces and configured to mate with the external surface of the post of the implant-abutment system, the internal surface having a tapered surface portion and a flat inner side wall for engaging the flat portion of the post to hold the impression coping non-rotationally on the post; and
   means for engaging a correspondingly shaped structure on the post of the implant-abutment system and axially holding the coping on the post, the axial engagement means being located such that at least a portion of the tapered surface portion is located below the axial engagement means and at least a portion of the tapered surface portion is located above a lower end of the axial engagement means, the portion of the tapered surface portion located below the axial engagement means being uninterrupted such that the lowermost surface is uninterrupted,
   wherein the at least a portion of the tapered surface portion located above the lower end of the axial engagement means engaging the tapered external surface of the post of the implant-abutment system.

2. The implant-abutment system of claim 1, wherein the at least one flange includes four outwardly extending flanges.

3. The implant-abutment system of claim 1, wherein the engagement means is a dimple adapted to receive the correspondingly shaped structure on the post.

4. The implant-abutment system of claim 1, wherein the engagement means is a recess adapted to receive a bump on the post.

5. The implant-abutment system of claim 1, wherein the lowermost surface includes an annular rim surface for abutting a corresponding annular support surface adjacent the bottom of the post.

6. The implant-abutment system of claim 5, wherein the annular rim surface is angled with respect to a central axis of the implant-abutment system.

7. The implant-abutment system of claim 1, wherein the impression coping is made of plastic.

8. An implant-abutment system, comprising:
   a supragingivally extending post being a unitary single-piece structure and having a top portion, a bottom portion, and an external surface, the external surface having a frustoconically shaped tapered wall and a flat wall, the top portion including a substantially flat top surface, the bottom portion including an angled annular support surface extending circumferentially therearound, and the post further including a first axial locking member on the external surface below the substantially flat top surface; and
   a plastic impression coping for engaging the post of the implant-abutment system, the impression coping including an uppermost portion, a lowermost portion, and an internal surface having a tapered wall and a flat wall, the lowermost portion including an angled annular rim for abutting the annular support surface of the post, the internal surface further including a second axial locking member for engaging the first axial locking member, the second axial locking member being located on the internal surface such that at least a portion of the tapered surface is located above a lower end of the second axial locking member, the at least a portion of the tapered surface located above the lower end of the second axial locking member engages at least a portion of the frustoconically shaped tapered wall of the post, one of the first and second axial locking members creating an undercut that receives a corresponding structure on the other of the first and second axial locking members.

9. The system of claim 8, wherein the second axial locking member is a dimple and the first axial locking member is a corresponding protrusion adapted to mate with the dimple.

10. The system of claim 8, wherein the second axial locking member is a recess and the first axial locking member includes a bump on the post adapted to mate with the recess.

11. The system of claim 8, wherein the uppermost portion of the impression coping includes an outwardly extending flange.

12. The system of claim 8, further including an implant-abutment analog having a supragingivally extending post analog member with a top portion, a bottom portion, and an external surface, the external surface having a tapered wall and a flat wall, the post analog member further including a third axial locking member on the external surface, the third axial locking member being substantially similar to the first axial locking member and for engaging the second axial locking member of the impression coping.

13. The system of claim 8, wherein the implant-abutment system includes an implant and an abutment, the abutment fitting within an axially extending bore of the implant and including the post.

14. The system of claim 8, wherein the second axial locking member is located on the internal surface such that at least a portion of the internal surface is located directly below the second axial locking member.

15. A method for taking an impression of an implant-abutment system having a supragingival post with an external side surface and a substantially flat top surface, the external side surface having a tapered wall and a flat wall, the post further including an impression coping engagement member along the external side surface below the substantially flat top surface, the method comprising:
- providing an impression coping, the impression coping having an uppermost portion, a lowermost portion, and an internal surface with a flat wall and a tapered wall, the internal surface further including an implant-abutment engagement member for engaging the impression-coping engagement member, the implant-abutment engagement member being located on the internal surface such that at least a portion of the tapered wall is located below the implant-abutment engagement member and at least a portion of the tapered wall is located above a lower end of the implant-abutment engagement member;
- snapping the impression coping onto the post of the implant-abutment system such that the impression-coping engagement member locks against the implant-abutment engagement member along the external side surface of the post and axially holds the impression coping on the implant-abutment system;
- applying impression material around the impression coping; and
- removing the impression material from the implant-abutment system such that the coping is removed with the impression material.

16. The method of claim 15, wherein at least one of the implant-abutment engagement member and the impression-coping engagement member includes an undercut region and the other of the implant-abutment engagement member and the impression-coping engagement member comprises a corresponding protruding portion, such that during the snapping the undercut region engages the corresponding protruding portion.

17. The method of claim 16, wherein the impression coping engagement member comprises the undercut region and the implant-abutment engagement member comprises the corresponding protruding portion.

18. The method of claim 17, wherein the undercut region is included in a bump and the protruding portion protrudes from a dimple configured to engage the bump.

19. The method of claim 15, wherein the implant-abutment engagement member is a dimple and the impression-coping engagement member is a corresponding protrusion adapted to mate with the dimple.

20. The method of claim 15, wherein the implant-abutment engagement member is a contoured hole and the impression coping engagement member includes a bump on the post, such that the snapping includes mating the contoured hole with the bump.

21. The method of claim 15, wherein the lowermost portion of the impression coping includes an internal rim surface with an annular shape.

22. The method of claim 21, wherein the post includes an annular shoulder, and the method further comprises abutting the internal rim surface against the annular shoulder.

23. The method of claim 22, wherein the internal rim surface ring and the annular shoulder are both angled with respect to a central axis of the implant-impression system.

24. The method of claim 15, wherein the uppermost portion includes an outwardly extending flange.

25. The method of claim 15, further comprising inserting an implant-abutment analog into the impression coping while the impression coping is encased in the impression material.

26. The method of claim 25, wherein the implant-abutment analog includes an impression coping engagement member, and the step of inserting the implant-abutment analog includes snapping the implant-abutment analog into the impression coping such that the impression coping engagement member of the implant-abutment analog locks against the implant-abutment engagement member of the impression coping and axially holds the impression coping onto the implant-abutment analog.

27. The method of claim 15, wherein the implant-abutment system includes an implant and an abutment, the abutment fitting within an axially extending bore of the implant and including the post, the abutment being a unitary, single-piece component.

28. The system of claim 15, wherein the implant-abutment engagement member is located on the internal surface such that at least a portion of the internal surface is located directly below the implant-abutment engagement member.

29. An implant-abutment system, comprising:
- an implant for engagement with bone and having an internal bore with a first tapered section;
- an abutment having an implant-engagement region and a supragingivally extending post region, said implant-engagement region having a second tapered section providing a locking-tapered engagement with said first tapered section of said implant, said supragingivally extending post region being a unitary single-piece structure and having a top surface, a bottom surface, and an external surface between said top surface and said bottom surface, said external surface having a frustoconically shaped tapered wall and a flat wall, said post region including a first axial locking member located on said external surface and below said top surface such that at least a portion of said external surface is located below said first axial locking member, said first axial locking member having a lowermost end that is located below at least a portion of said tapered wall; and
- a plastic impression coping fitting over said post region of said abutment, said impression coping including an uppermost portion, a lowermost portion, and an internal surface having a tapered surface and a flat surface, said internal surface further including a second axial locking member located on said internal surface such that at least a portion of said internal surface is located directly below said second axial locking member and at least a portion of said tapered surface is located above a lower end of said second axial locking member, said second axial locking member engaging said first axial locking member of said post region of said abutment and locking said plastic impression coping on said abutment.

30. The system of claim 29, wherein said first axial locking member is a structure extending from said external surface.

31. The system of claim 30, wherein said structure is a retention bump on said external surface and said second axial locking member is a dimple for receiving said retention bump.

32. The system of claim 30, wherein said structure is located on said flat surface.

33. The system of claim 29, wherein said first axial locking member is located on said flat surface.

34. The system of claim 29, wherein said flat wall and said flat surface mate to resist relative rotation of said impression coping and said abutment.

35. The system of claim 29, wherein the uppermost portion of the impression coping includes an outwardly extending flange.

36. The system of claim 29, further including an implant-abutment analog having a supragingivally extending post analog member that is shaped similar to said post region and includes a third axial locking member, the third axial locking member being substantially similar to the first axial locking member and for engaging the second axial locking member of the impression coping.

* * * * *